US011718827B2

(12) United States Patent
Jiao et al.

(10) Patent No.: US 11,718,827 B2
(45) Date of Patent: Aug. 8, 2023

(54) LRFFT2 CELL

(71) Applicants: BEIJING DCTY BIOTECH CO., LTD., Beijing (CN); Shunchang Jiao, Beijing (CN)

(72) Inventors: Shunchang Jiao, Beijing (CN); Rong Zhang, Beijing (CN); Tianfu Zhang, Beijing (CN); Zishan Zhou, Beijing (CN); Jiasen Xie, Beijing (CN); Ziming Wu, Beijing (CN); Gang Peng, Beijing (CN)

(73) Assignees: Beijing DCTY Biotech Co., Ltd., Beijing (CN); Shunchang Jiao, Beijing (CN)

( * ) Notice: Subject to any disclaimer, the term of this patent is extended or adjusted under 35 U.S.C. 154(b) by 759 days.

(21) Appl. No.: 16/508,740

(22) Filed: Jul. 11, 2019

(65) Prior Publication Data
US 2020/0102537 A1  Apr. 2, 2020

(30) Foreign Application Priority Data
Sep. 30, 2018 (CN) .......................... 201811153257.5

(51) Int. Cl.
| *C12N 15/85* | (2006.01) |
| *C12N 5/0783* | (2010.01) |
| *C07K 14/725* | (2006.01) |
| *C12N 7/00* | (2006.01) |
| *C12N 15/11* | (2006.01) |
| *C12N 15/86* | (2006.01) |
| *G01N 33/50* | (2006.01) |

(52) U.S. Cl.
CPC ........ *C12N 5/0636* (2013.01); *C07K 14/7051* (2013.01); *C12N 7/00* (2013.01); *C12N 15/11* (2013.01); *C12N 15/86* (2013.01); *G01N 33/505* (2013.01); *C12N 2310/20* (2017.05); *C12N 2501/998* (2013.01); *C12N 2502/11* (2013.01); *C12N 2510/00* (2013.01); *C12N 2740/15043* (2013.01)

(58) Field of Classification Search
None
See application file for complete search history.

(56) References Cited

U.S. PATENT DOCUMENTS

| 2020/0123220 A1* | 4/2020 | Bonini ............... C07K 14/4748 |
| 2020/0223899 A1* | 7/2020 | Veatch ..................... C12N 7/00 |

FOREIGN PATENT DOCUMENTS

| CN | 103242448 B | 1/2015 |
| CN | 104926944 A | 9/2015 |
| CN | 107074932 A | 8/2017 |
| WO | WO-2016053338 A1 * | 4/2016 ......... A61K 39/0011 |

OTHER PUBLICATIONS

First Office Action issued by the China National Intellectual Property Administration (CNIPA) dated Apr. 14, 2020 regarding Chinese application No. 201811153257.5, Beijing, China.

* cited by examiner

*Primary Examiner* — Celine X Qian
(74) *Attorney, Agent, or Firm* — Avek IP, LLC

(57) ABSTRACT

Some embodiments of the disclosure use human peripheral blood for ctDNA sequencing or tumor tissues for whole exome sequencing, screen out mutation sites to perform antigen epitope prediction, connect and synthesize an expression gene sequence of mutant peptides. Other embodiments of the disclosure construct a lentiviral vector, package the lentivirus, transfect an APC cell to complete transformation of a specific LV cell, co-culture in vitro with PBMC separated from the peripheral blood, screen out an effective polypeptide, and transform common T cells into RFF cells. Suppressive signaling molecules include one or more of PD-1, Tim-3, LAG3, CTLA-4, BTLA, VISTA, CD160, and 2B4 (CD244). Antigen presenting cells include one or more of PBMC, a dendritic cell, neutrophil, B lymphocyte, and macrophage.

5 Claims, 6 Drawing Sheets
Specification includes a Sequence Listing.

LRFFT2 CELL

CROSS REFERENCE TO RELATED APPLICATIONS

This application claims priority to Chinese application number 201811153257.5 filed on Sep. 30, 2018, the disclosure of which is incorporated by reference herein in its entirety.

FIELD OF THE DISCLOSURE

The disclosure relates generally to the field of biotechnologies. More specifically, the disclosure relates to an LRFFT2 cell and a preparation method thereof.

BACKGROUND

At present, in the specific immunotherapy of tumors, the existing LAK, DC, CIK, and DC-CIK cell therapies and methods have basically proved to be ineffective, while cell technologies such as NK, CAR-NK, and TIL are not mature yet, and CAR-T cells are also defective in the safety and treatment of solid tumors. Some prior art references disclose producing specific cytotoxicity by transforming DC cells and presenting T cells with DC cells. Some laboratories are attempting to transfect the presenting T cells by using a virus as a vector to induce the specific cytotoxicity of the T cells. We have also directly stimulated Peripheral Blood Mononuclear Cell (PB MC) and induced the T cells with mixed mutant peptides. There are also laboratories that use the TCR-T technology to target cells presenting MAGE A3 antigens.

The foregoing treatment methods are not mature, especially the induction of DC cells in vitro and technologies for bearing tumor antigens with DC cells are theoretically studied, but there are still many problems in the specific implementation process, lack of clear related molecules of signaling pathways for tumor cell development and progression acts as inducing antigens, because of unknown tumor antigens and barriers of tumor microenvironmental immunosuppression, which makes it difficult to implement specific cell-targeted immunotherapy. In addition, although some antigen stimulation in vitro have been carried out, co-culture and expansion in vitro have not been carried out, so that relatively thin specific cells directly face the complex tumor immune microenvironment, and therefore, it is difficult to achieve the desired effect. Some may also be presented in vitro and co-cultured, but the target is single (MAGE-3), which only works for limited types of cancers such as the non-small cell lung cancer. Although it is also attempted to transfect and present by using a lentivirus as the vector, the safety and convenience are inferior to the polypeptide. Moreover, direct stimulation of polypeptide is simply mixed, although it is simple and convenient, the efficiency is low. The effect of secondary stimulation of specific precise polypeptide is less direct than that of tumor-specific antigens transduced by T cell receptors. The existing TCR-T lacks a precise TCR covering more types of tumors in the solutions for treating hematological and solid tumors.

None of the foregoing solutions consider the self-protection technology of T cells. As a result, a small number of specific T cells directly face the powerful tumor immune microenvironment. There is a general lack of accurate and effective analysis of patient antigens.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

Some embodiments of the disclosure use peripheral blood of a patient for ctDNA sequencing or tumor tissues for whole exome sequencing, screen out mutation sites to perform antigen epitope prediction, and connect and synthesize an expression gene sequence of mutant peptides. Other embodiments of the disclosure construct a lentiviral vector, package the lentivirus, transfect an APC cell to complete transformation of a specific LV cell, co-culture in vitro with PBMC separated from the peripheral blood, screens out an effective polypeptide, transform common T cells into RFF cells with more precise killing ability through the second stimulation of precise effective polypeptide, and transform by using the TCR-T technology principle. The transformed T cells block immunosuppressive signaling molecules with antibodies in vitro, which protects the specific killing T cells from inhibition in vivo and improves the killing ability of T cells to tumor cells.

In some embodiments, an LRFFT2 cell transformation scheme includes the following steps.

1. Antigen Epitope Prediction

Human peripheral blood is used for ctDNA sequencing or commercially available engineering cell lines (e.g., H1299, H226, H358, H1563, H2228, A549, Renca, LLC mouse Lewis lung cancer cells, CRL-6323 B16F1, CRL-2539 4T1, U14 mouse cervical cancer cells, BV-2 mouse microglioma cells, G422 mouse glioma cells, etc.) are subjected to MHC type detection and whole exome sequencing to detect RNA mutations. MHC type and gene mutation information are used to predict an antigen epitope: the antigen epitope prediction is centered on a mutant amino acid site, extends 8 amino acids to each side, and the polypeptide segment having 17 amino acids is used as a potential antigen epitope. IC50 of the potential antigen epitope is analyzed by using prediction software, and if the IC50<1,000 nM, the potential antigen epitope is considered to be an antigen epitope.

2. Polypeptide Connection

The foregoing software is used to analyze the IC50 of a joint after the connection of any two antigen epitopes, the antigen epitope is considered to be weak immunogenic and can be connected when IC50≥1,000 nM, and the antigen epitope is considered to be strong immunogenic and cannot be connected when IC50<1,000 nM. According to the foregoing results, the weak immunogenic antigen epitopes are connected together, and the IC50 of the joint is higher than the IC50 of the antigen epitope on both sides (that is, it should avoid generating strong binding antigen at the joint as much as possible).

3. Synthesis of the Gene Sequence of Connected Peptides

The connected peptides are converted to a nucleotide sequence to perform codon optimization. The gene sequence of the antigen epitope peptide is synthesized by a technology service company.

4. Lentivirus Package

The gene sequence synthesized in the previous step is constructed into a lentiviral expression plasmid expressing the antigen epitope peptide, and then lentivirus package is performed.

5. Transfection of an Antigen Presenting Cell (APC) and Co-Culture with PBMC

The APC (including, but not limited to, one or more of the PBMC, a dendritic cell, neutrophil, B lymphocyte, and macrophage) is transfected by a lentivirus expressing the antigen epitope peptide. The processed APC is collected, and the APC and PBMC are mixed and co-cultured at a ratio of 1:5-20 to obtain an effector cell.

6. Screening of Effective Precise Polypeptide, and Stimulation of T Cells Again with Precise Polypeptide The T cells obtained by the foregoing solution are centrifugally collected, and the polypeptide is used as an antigen to directly stimulate the T cells to screen the precise polypeptide. A positive control: T cells+100 ng/mL OKT3 is set, and a negative control: T cells+1640+10% FBS+200 U/mL IL2 is set. Evaluation criteria of the precise polypeptide are: if the positive control and the negative control are reasonable, the data is reliable; and if an experimental group is significantly larger than the negative control group, the polypeptide is an effective precise polypeptide. Secondary stimulate is performed on the T cells with the screened precise polypeptide.

7. Construction of TCR-T Cells

The stimulated T cells are stained with CD8, CD137, IFN-γ, and are sorted by a flow cytometer. Specific cells capable of identifying the precise polypeptide are sorted, and the high-frequency TCR sequences are determined by sequencing and are amplified. A TCR gene expression vector is constructed, and the lentivirus is packaged. The TCR gene is capable of specifically binding to the precise polypeptide to obtain a TCR-T cell. The original TCR gene in the peripheral blood T cells is knocked out, and is transferred into the TCR gene constructed in the previous step for culture to obtain the TCR-T cells.

8. Blocking of Immunosuppressive Signaling In Vitro with the Antibody to Obtain the LRFFT2 Cell The cell surface suppressive signaling molecule includes one or more of PD-1, Tim-3, LAG3, CTLA-4, BTLA, VISTA, CD160, and 2B4 (CD244).

9. Construction of specific antigen-expressing target cells and tumor model survival experiments.

DETAILED DESCRIPTION

Figure 1A:
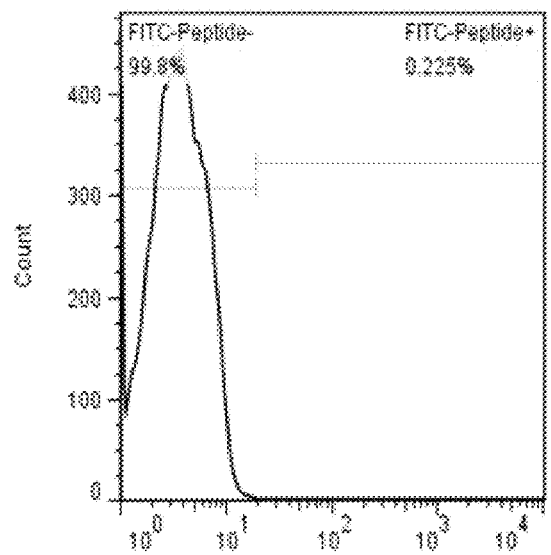
FIG. 1A shows lentiviral transfection APC efficiency detection of a control group.

The following describes multiple exemplary embodiments of the disclosure with reference to the accompanying drawings in the embodiments of the disclosure. The described embodiments are merely a part rather than all of the embodiments of the present invention. All other embodiments obtained by a person of ordinary skill in the art based on the embodiments of the present invention without creative efforts shall fall within the protection scope of the present invention.

Regarding the term "LRFFT2" in the disclosure, "L" represents lentiviral transfection technology, "R" represents secondary stimulate technology for precise polypeptide, "FF" represents mixed peptides technology, "T" represents TCR-T technology, and "2" represents antibody blocking protection technology in vitro. According to an embodiment, an LRFFT2 cell means a cell obtained by transformation of one or more of various technical schemes or technical means of L, R, FF, T, and 2 described above.

In some embodiments, the technical scheme includes the following steps.

1. Antigen Epitope Prediction

The peripheral blood of a patient with lung cancer is used for ctDNA sequencing and HLA subtype detection. The sequencing information is analyzed with bioinformation software, the ctDNA sequencing result is compared with a genome of normal cells, and mutation sites are screened out. The antigen epitope prediction is centered on a mutant amino acid site, extends 8 amino acids to each side, and the polypeptide segment having 17 amino acids is used as a potential antigen epitope. IC50 of the potential antigen epitope is analyzed with prediction software (recommended software: NetMHCpan 3.0, PickPocket, and Artificial Neural Networks (ANN)), and if IC50<1,000 nM, this potential antigen epitope is considered to be an antigen epitope.

2. Polypeptide Connection

The foregoing software is used to analyze the IC50 of a joint after the connection of any two antigen epitopes, the antigen epitope is considered to be weakly immunogenic and can be connected when IC50≥1,000 nM, and the antigen epitope is considered to be strong immunogenic and cannot be connected when IC50<1,000 nM. Here the IC50 calculation results of three prediction software should be considered, the antigen epitope is considered to be weakly immunogenic when the IC50≥1,000 nM calculated by ≥2 software, and the antigen epitope is considered to be strong immunogenic when IC50<1,000 nM calculated by ≥2 software. According to the foregoing results, the antigen epitopes are connected together, and the IC50 at the joint is higher than the IC50 of the antigen epitopes on both sides (that is, it should avoid generating strong binding antigen at the joint as much as possible.) If necessary, the weak immunogenic peptide is used as a linker peptide to space the strong immunogenic peptide, or the patient's own amino acid is added to the joint to reduce the probability of producing a strong antigen.

3. Synthesis of the Gene Sequence of Connected Peptides

The connected polypeptide is converted to a nucleotide sequence to perform codon optimization. If the nucleotide sequence after the completion of connection is short (<100 bp), the amino acid sequence can be appropriately repeated once again. However, it should be noted that during conversion to a gene sequence, the occurrence of an inverted repeat sequence, a direct repeat sequence, and a mirror repeat sequence in the gene sequence should be avoided as much as possible. The gene sequence of the antigen epitope peptide is synthesized by a technology service company).

4. Lentivirus Package 4.1. The gene sequence of the synthesized antigen epitope peptide is cloned into a pCDH-MSCV-MCS-EF1-copGFP plasmid to construct a lentiviral expression plasmid expressing the antigen epitope peptide.

4.2. Lentivirus Package 4.2.1. Recovery of 293T cells which are passed for two generation for lentivirus package.

4.2.2. Cell transfection (T175 culture flask)

A 15 mL centrifuge tube (labeled as A) is taken, 400 μL of Lipofectamine 2000 is gently added to 4 mL of DMEM, gently mixed, and stand at room temperature for 5 min. Another two 15 mL centrifuge tubes (labeled as B and C, B for the control group, and C for the experimental group) are taken, the following reagents are added and gently mixed, and stand at room temperature for 5 min.

| | Reagent name | Number of reagents |
|---|---|---|
| Tube B | Control plasmid (0.23 μg/μL) | 34.8 μL |
| | Packaging plasmid mix (1 μg/μL) | 24 μL |
| | DMEM | 1.75 mL |
| Tube C | pCDH-MSCV-MCS-EF1-copGFP plasmid containing target genes (1.95 μg/μL) | 4.1 μL |
| | Packaging plasmid mix (1 μg/μL) | 24 μL |
| | DMEM | 1.75 mL |

Liquid in tube A is transferred into the tube B and the tube C on average, gently mixed, and stand at room temperature for 20 min. An old medium in T175 is poured out, the cells are washed with PBS, new 25 mL of DMEM (without antibiotics and serum) is replaced, gently added with a mixed liquor of A and B or a mixed liquor of A and C, shaken gently, and cultured in a 5% $CO_2$ incubator at 37° C. The medium containing a transfection complex is absorbed after transfection for 6 h, replaced with fresh medium preheated at 37° C., cultured for 48 h, and collected.

4.2.3. Lentivirus Concentration and Titer Determination

The lentivirus supernatant is collected after the lentivirus packaging is successful, and lentivirus supernatant is centrifuged at 4° C. in 4,000 g for 10 min. The supernatant is filtered with a 0.45 μm filter to remove cell debris. The virus supernatant and a concentrated reagent are mixed according to a ratio of 5:1, and placed at 4° C. for 2 h or overnight. Incubated mixture is centrifuged at 4° C. in 4,000 g for 30 min, so that creamy white precipitates at the bottom of the tube can be seen. The supernatant is carefully removed (do not touch the precipitates.) An appropriate volume of DMEM or PBS is added, and the precipitates are gently blown and resuspended. The virus is subpackaged as needed, and stored at −80° C. (note: lentivirus should not be frozen and thawed repeatedly, and the titer of lentivirus will decrease by 10%-20% every freeze-thaw).

The 293H cells in good growth state are digested, counted and diluted to $5 \times 10^4$/mL one day before determination, and added to a 96-well plate at 100 μL/well to prepare 8-10 wells for each virus. The 96-well plate is placed in a 5% $CO_2$ incubator at 37° C. A certain amount of cells infected with the virus solution is taken, and diluted in an EP tube at a 10-fold gradient. The dilution method is as follows: ten 1.5 mL EP tubes are prepared for each virus, 90 μL of culture solution is added to each tube, and 10 μL of the virus stock solution is added to the first tube, which is marked as $10^0$. Ater mixing, 10 μL of the solution is taken to be added to the second tube for mixing, which is recorded as $10^{-1}$, and so on ($10^0$-$10^{-8}$). 10 μL of diluted virus solution is added to the corresponding cell wells and marked, and the results are observed after culturing for 48-72 h.

Titer calculation: for the lentivirus with fluorescent labeling, titer can be determined using the fluorescence technique. The results are observed under a fluorescence microscope, and the number of fluorescent cell clones of the last two fluorescent lentivirus is counted, assumed to be X and Y, then the titer (TU/mL)=(X+Y×10)×1000/2/X well of the virus solution content (μL).

5. Transfection of APC with Lentivirus and Co-Culture with PBMC

A whole cell culture medium containing 300 U/mL rIL-2 and 10% FBS is prepared by using RPMI-1640, marked as RPMI-10-IL-2. The APC cell concentration is adjusted to $1 \times 10^6$/mL by using the RPMI-10-IL-2. A lentivirus expressing an antigen epitope peptide is used to infect the APC with MOI=5-20 (including, but not limited to, one or more of the PBMC, the dendritic cell, neutrophil, B lymphocyte, and macrophage), and cultured for 72 h at 37° C. The processed APC is collected, the APC is mixed with the PBMC at a ratio of 1:5-20, the PBMC is about $5 \times 10^7$, 50 mL of OKM100 culture medium is added to the T75 culture flask. Put in a cell incubator to be cultured at 30-37° C. for 14 days, to obtain the effector cells of the LFF scheme.

6. Screening of Effective Precise Polypeptide

The polypeptide is used as an antigen to directly stimulate the effector cells to screen the precise polypeptide. The cells of the foregoing LFF scheme are collected centrifugally, and the T cells are centrifugally collected at 1,500 rpm for 5 min. 10 mL of PBS is added for resuspending the cells, and counted, centrifuged at 1,500 rpm for 5 min, and the T cells are collected and resuspended in 1640+10% FBS+200 U/mL IL2, and the count is adjusted to 1×10 6 cells/mL. The T cells are distributed into a 96-well flat-bottom plate at 200 μL/well with a gun, and the number of cells is $2 \times 10^5$ cells. Then 10 μL of 1 mg/mL mutant peptides is added, and a final concentration is 50 μg/mL, each polypeptide is replicated with 3 wells. A positive control: T cells+100 ng/mL OKT3 is set, and a negative control: T cells+1640+10% FBS+200 U/mL IL2 is set. The flat-bottom plate is stimulated in 5% $CO_2$ at 37° C. for 24 h, centrifuged at 1,500 rpm for 10 min, and 140 μL of supernatant is transferred to a new 96-well plate. The 96-well plate is centrifuged at 1,500 rpm for 10 min, and a sample is taken for ELISA detection (or the sample is placed at −80° C. for storage).

ELISA System for Detecting IFN-γ

ELISA kits currently available for detection of IFN-γ include Biolegend: LEGEND MAX Human IFN-7 ELISA Kit with Pre-coated Plates (Cat. No. 430107) and Dakewe: Human IFN-γ ELISA Kit (Cat. No.: DKW12-1000-096), please strictly follow the manufacturer's instructions. An ELISA manual plate packaging system (15 plates): Human IFN-gamma DuoSet 15 plate (Cat. No. DY285B)×1, DuoSet ELISA Ancillary Reagent Kit 2 (Cat. No.: DY008)×3.

Precise Peptide Evaluation Criteria

If the positive control and the negative control are reasonable, the data is reliable. If an experimental group is significantly larger than the negative control group, the polypeptide is an effective precise polypeptide.

7. Secondary Stimulate on the T Cells with the Screened Precise Polypeptide

PBMC is cultured with step 5 to the 2nd to 14th day, $2 \times 10^7$ effector cells are taken, and the precise polypeptide with a final concentration of 10 μg/mL-100 μg/mL is added to stimulate for 1-4 h. The mixture is transferred to the 6-well plate of OKM25 pre-coated plate or T25 cm² culture flask after 4 h of stimulate, OKM100+12% FBS are supplemented, cultured in 5% CO₂ at 37° C., transferred to T75 culture flask according to cell growth, and the cell density is kept at 1×10⁶ cells/mL as much as possible. In the T175 culture flask, the culture medium is OKM200+5% FBS, and the T cells, i.e., the LRFF cells, obtained by secondary stimulate of precise polypeptide can be obtained in 10-14 days of culture.

8. Culture and Separation of Mutant Antigen Specific Killing T Cells

The LRFF cells obtained in step 7 are stimulated by directly using the screened precise polypeptide as antigen stimulation for 12-72 h for standby. The stimulated T cells are stained with CD8, CD137, IFN-γ, and are sorted by a flow cytometer, and CD8+CD137+ or CD8+IFN-γ+ cells are selected.

9. TCR Frequency Detection of CD8+ T Cells and Cloning of High-Frequency TCR

The genome of the sorted CD8+CD137+, or CD8+IFN-γ+ cells is extracted, TCR frequency detection is performed, and a high-frequency TCR sequence is determined. The mRNA of the sorted cells is extracted, reversely transcript into cDNA, and primers are designed according to the high-frequency TCR sequence, and amplified to obtain the TCR gene. A TCR gene expression vector is constructed, and the lentivirus is packaged.

10. Construction of TCR-T Cells

PBMC is recovered and CD8+ cells are sorted with magnetic beads for standby. Gene knockout is performed on the original TCR of CD8+ T cells with the CRISPR technology, and if no TCR expression is detected, the CD8+ T cells are transferred into the constructed TCR expression vector. The CD8+T cells transferred into the TCR gene are amplified and cultured, and the TCR-T cells are obtained after cultured to 10-21 days.

11. Blocking of Immunosuppressive Signaling

The immunosuppressive signaling molecule includes one or more of PD-1, Tim-3, LAG3, CTLA-4, BTLA, VISTA, CD160, and 2B4 (CD244). Centrifugation is performed at 1,000 rpm for 5 min to collect the cultured TCR-T cells. The TCR-T cells are washed once with PBS and centrifuged at 1,000 rpm for 5 min, the TCR-T is resuspended with OKM-200+5% FBS, and adjusted to 1×10⁷/mL. A monoclonal antibody (such as PD1/PDL1 antibody) of suppressive signaling molecule is added at a final concentration of 50-200 µg/mL, preferably 150 µg/mL, and blocked for 1-4 h at 0-37° C., preferably for 1 h at 37° C., to obtain the LRFFT2 cell.

12. Construction of Specific Antigen-Expressing Target Cells and Tumor Model Survival Experiments A lentiviral vector that can express the screened precise polypeptide (specific antigen) is constructed. The specific antigen-expressing lentiviral vector is packaged into lentiviral particles, appropriate HLA-matched tumor cells are infected, specific antigen are stably overexpressed, and the expression level and expression intensity are detected by flow cytometry. Tumor cell lines stably overexpressing specific antigen peptides are inoculated with NGS mice to make an ectopic tumor-bearing animal model. 5×10⁵ tumor cells expressing the specific antigen are suspended in 100 µl of physiological saline, subcutaneously injected into the right flank of 30 NSG mice, and the mice are numbered. The cells are returned to the group when the tumor grows to about 100-120 mm³. According to the tumor volume, the animal model is randomly divided into three groups, each group of 5-6 mice, one group is given placebo saline, one group is given 1×10⁷ of T cells (control group) without any genetic manipulation, and one group is given 1×10⁷ of LRFFT2 cells, the second injection is performed 7 days after the first injection of cells, and the cells are injected for the third time after 7 days, observation is made for 60 days continuously, the survival data is counted, and the survival curve is plotted.

Test Results

1. Mutation Site and Antigen Epitope Prediction

Table 1 shows a prediction result of mutation sites and antigen epitopes detected by sequencing.

TABLE 1

| Antigen epitope prediction | | |
|---|---|---|
| Polypeptide No. | Antigen epitope | Affinity with HLA (nM) |
| 1 | SSMQTGMNL (SEQ ID NO: 1) | 15.5 |
| 2 | AVGKHTLK (SEQ ID NO: 2) | 34.77 |
| 3 | IVIPNDGLY (SEQ ID NO: 3) | 33.3 |
| 4 | YMFQRNVNSVL (SEQ ID NO: 4) | 18.17 |
| 5 | ASDVDYCVAK (SEQ ID NO: 5) | 32.4 |
| 6 | NMAVGKHTLK (SEQ ID NO: 6) | 240.35 |
| 7 | FVNVTFQMK (SEQ ID NO: 7) | 75.79 |
| 8 | VLMPTKAV (SEQ ID NO: 8) | 57.82 |
| 9 | TQFVNVTFQMK (SEQ ID NO: 9) | 91.58 |
| 10 | QPIEWVKDTY (SEQ ID NO: 10) | 16.22 |
| 11 | QASSPPVGIPM (SEQ ID NO: 11) | 30.21 |
| 12 | KLATRYVFQI (SEQ ID NO: 12) | 21.2 |

2. Lentivirus Transfection APC Efficiency Detection

Figure 1B:
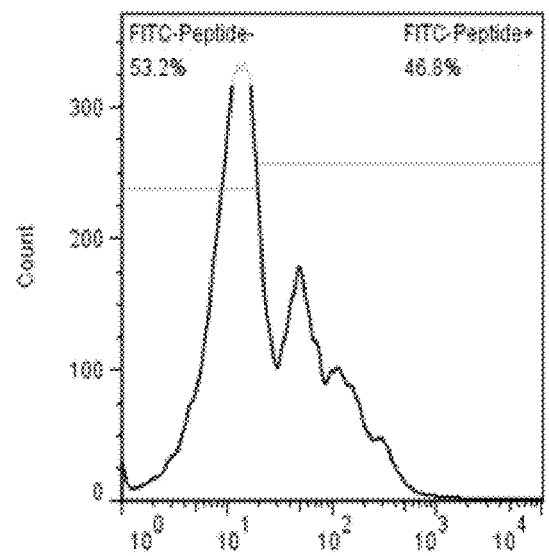
FIG. 1B shows lentiviral transfection APC efficiency detection of a transfection group.

A whole cell culture medium containing 300 U/mL rIL-2 and 10% FBS is prepared by using RPMI-1640, marked as RPMI-10-IL-2. The APC cell concentration is adjusted to 1×106/mL by using the RPMI-10-IL-2. A lentivirus expressing an antigen epitope peptide is used to infect the APC with MOI=5-20 (including, but not limited to, one or more of the PBMC, the dendritic cell, neutrophil, B lymphocyte, and macrophage), and cultured for 72 h at 37° C. The proportion of GFP positive in APC is detected by flow cytometer (as shown in FIGS. 1A & 1B).

3. LFF Cell Subtype Detection

Figure 2:
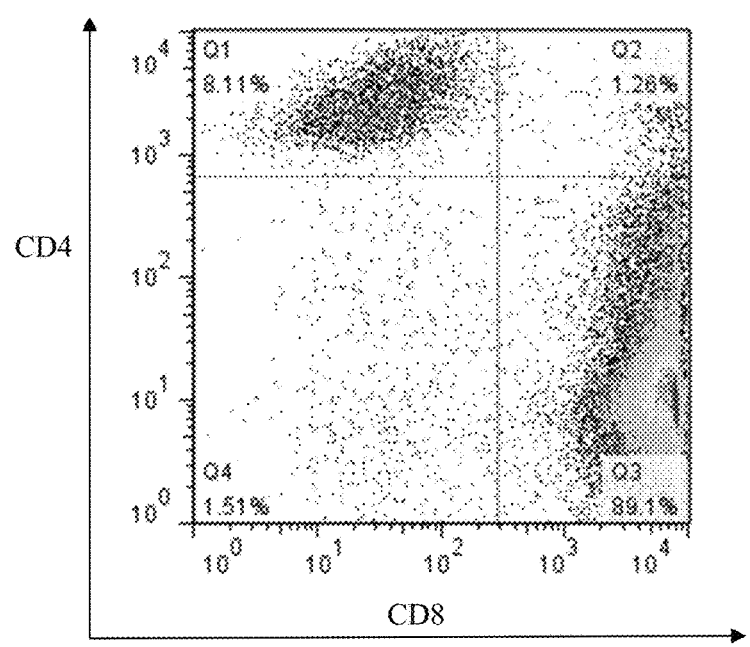
FIG. 2 shows LRFF cell subtype detection.

The subtype of CD4+ and CD8+ cells is performed after the cell culture of the LFF scheme. The results are as shown in FIG. 2: CD8+ T cells are 89.1%, and CD4+ T cells are 8.11%.

4. Screening for Precise Polypeptides with LFF Cells

Figure 3:
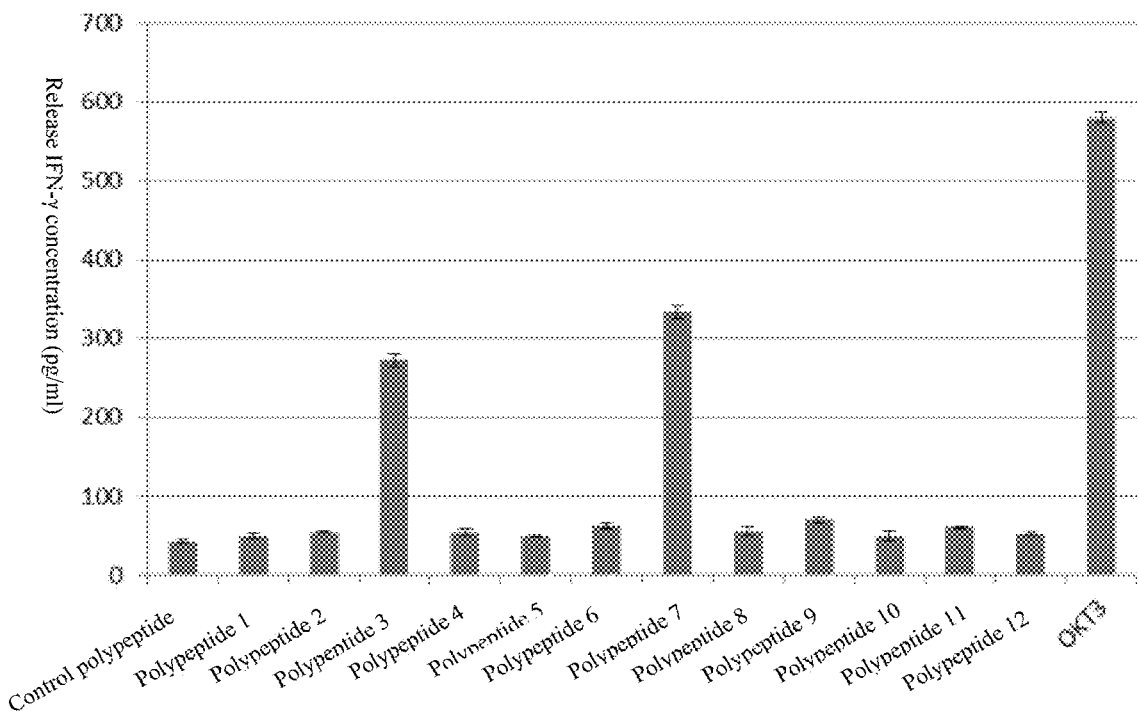
FIG. 3 shows screening of precise polypeptide.

The T cells are stimulated with 12 polypeptides, and the effective polypeptides are detected by detecting the secretion of IFN-γ. The results are as shown in FIG. 3: the release amount of IFN-γ by No. 3 and No. 7 polypeptides>the release amount of negative control, which is an effective precise polypeptide.

5. Identification and Sorting of Specific T Cells for Precise Polypeptides

Figures 4A, 4B:
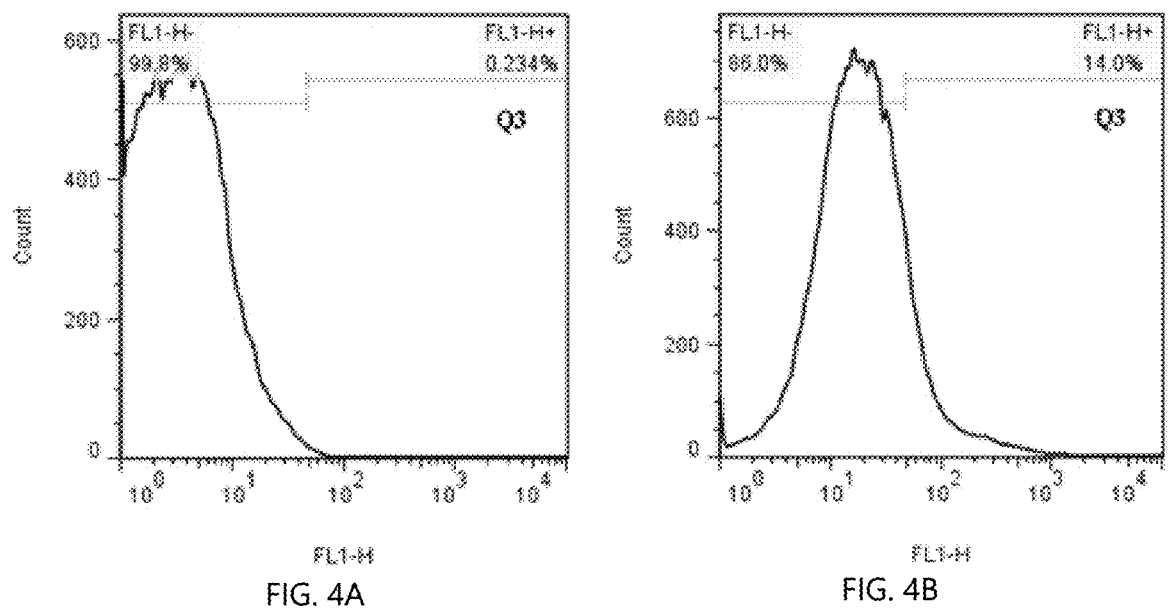
FIG. 4A shows a control group of flow cytometry detection of specific T cell ratio.
FIG. 4B shows an LRFF scheme of flow cytometry detection of specific T cell ratio.

The cells of the LFF scheme are stimulated by the selected No. 3 and No. 7 polypeptides, and the ratio of specific T cells for the precise polypeptides is detected by flow cytometry. The results are as shown in FIGS. 4A & 4B. FL1+ is a specific T cell: the cells of the LRFF scheme, the proportion of cells releasing IFN-γ caused by polypeptide No. 3 and No. 7 is significantly higher than that of cells without stimulation (control), indicating that the LRFF scheme can obtain specific T cells for precise polypeptides. Sorting of the CD8+ IFN-γ+ cells (FL1+) is performed by the flow cytometer.

6. Identification and Cloning of High-Frequency TCR

Figure 5:
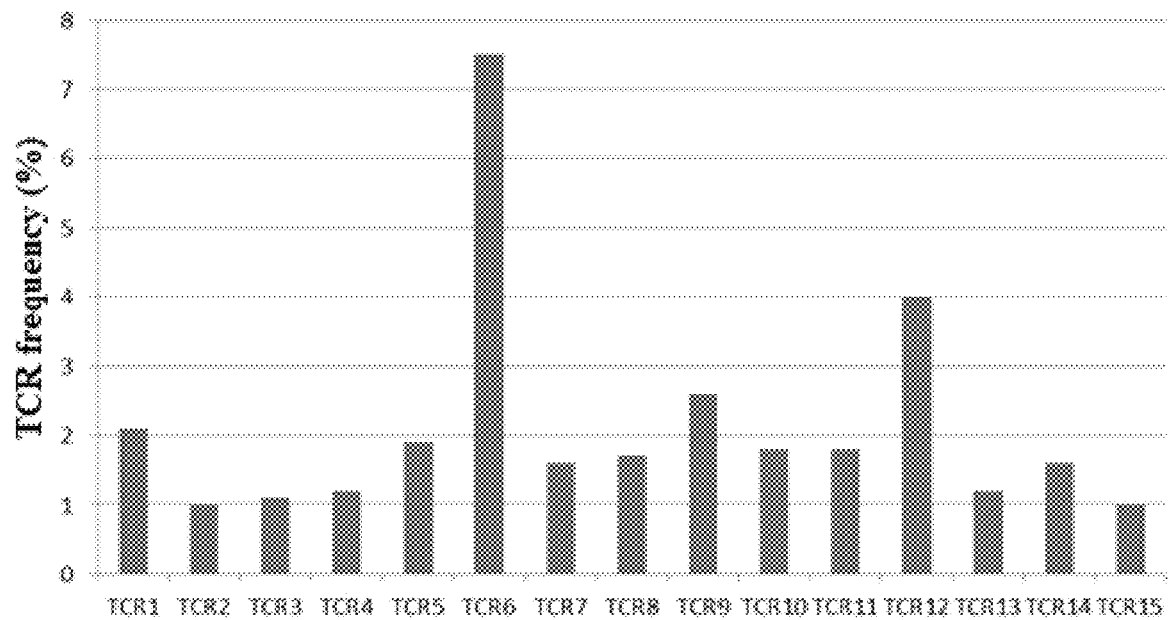
FIG. 5 shows TCR frequency.

Genome extraction on the sorted cells, sequencing of TCR, and the distribution of TCR are as shown in FIG. 5 (the top 20 of the high-frequency distribution), and the frequency of TCR6 distribution is high, indicating that the TCR is closely related to the mutant antigen, TCR is amplified according to the TCR sequence, to construct a lentiviral expression vector.

TABLE 2

Sequence of TCR β chain CDR3

| No. | CDR3 DNA sequence | CDR3 amino acid sequence |
| --- | --- | --- |
| TCR1 | TGTGCCAGCAGTCTCACCCTCACCTACGAGCAGTACTTC (SEQ ID NO: 13) | CASSLTLTYEQYF (SEQ ID NO: 14) |
| TCR2 | TGTGCCAGCAGCACCGAAAGACCCGAGCAGTACTTC (SEQ ID NO: 15) | CASSTERPEQYF (SEQ ID NO: 16) |
| TCR3 | TGTGCCAGTAGTATTGGGGCAGGTTTCCATCTCGAGCAGTACTTC (SEQ ID NO: 17) | CASSIGAGFHLEQYF (SEQ ID NO: 18) |
| TCR4 | TGTGCCAGCAGTTTATCGGCGGGACTGGGTGAGCAGTACTTC (SEQ ID NO: 19) | CASSLSAGLGEQYF (SEQ ID NO: 20) |
| TCR5 | TGTGCCAGCAGTGATTGGCCCTTGAATGAGCAGTTCTTC (SEQ ID NO: 21) | CASSDWPLNEQFF (SEQ ID NO: 22) |
| TCR6 | TGTGCCAGCAGTTTGGGGGGGTCGACACCCCTCCACTTT (SEQ ID NO: 23) | CASSLGGSTPLHF (SEQ ID NO: 24) |
| TCR7 | TGTGCCAGCAGTTTGGCGGGAGGGCCTAGCACAGATACGCAGTATTTT (SEQ ID NO: 25) | CASSLAGGPSTDTQYF (SEQ ID NO: 26) |
| TCR8 | TGCGCCAGCAGCCCAGCGAGAATCGGGGGGAGCACAGATACGCAGTATTTT (SEQ ID NO: 27) | CASSPARIGGSTDTQYF (SEQ ID NO: 28) |
| TCR9 | TGCGCCAGCAGCCAGACAGGGGCGAACTCCGAGCAGTACTTC (SEQ ID NO: 29) | CASSQTGANSEQYF (SEQ ID NO: 30) |
| TCR10 | TGTGCCAGCAGTGAAGGCGGGGACACCGGGGAGCTGTTTTTT (SEQ ID NO: 31) | CASSEGGDTGELFF (SEQ ID NO: 32) |
| TCR11 | TGTGCCAGCAGCGTAGGGGGGGATTATGGCTACACCTTC (SEQ ID NO: 33) | CASSVGGDYGYTF (SEQ ID NO: 34) |
| TCR12 | TGTGCCAGCAGCTTATCGGAGGGTACTGAAGCTTTCTTT (SEQ ID NO: 35) | CASSLSEGTEAFF (SEQ ID NO: 36) |
| TCR13 | TGTGCCAGCAGCTTCCCGGATGAGGGGGACTATGGCTACACCTTC (SEQ ID NO: 37) | CASSFPDEGDYGYTF (SEQ ID NO: 38) |
| TCR14 | TGCAGCGTTGTGGCACTAGCGGGAGGGCGGACCTCCTACGAGCAGTACTTC (SEQ ID NO: 39) | CSVVALAGGRTSYEQYF (SEQ ID NO: 40) |
| TCR15 | TGTGCCAGCTCACCACGGGACAGGGGGCTTACTAACTATGGCTACACCTTC (SEQ ID NO: 41) | CASSPRDRGLTNYGYTF (SEQ ID NO: 42) |

```
Known TCR-α:
Amino acid sequence:
                                            (SEQ ID NO: 43)
MMKSLRVLLV ILWLQLSWVW SQQKEVEQNS GPLSVPEGAI

ASLNCTYSDR GSQSFFWYRQ YSGKSPELIM FIYSNGDKED

GRFTAQLNKA SQYVSLLIRD SQPSDSATYL CAVNFGGGKL

IFGQGTELSV KPN

Base sequence:
                                            (SEQ ID NO: 44)
ATGATGAAAT CCTTGAGAGT TTTACTAGTG ATCCTGTGGC

TTCAGTTGAG CTGGGTTTGG AGCCAACAGA AGGAGGTGGA

GCAGAATTCT GGACCCCTCA GTGTTCCAGA GGGAGCCATT

GCCTCTCTCA ACTGCACTTA CAGTGACCGA GGTTCCCAGT

CCTTCTTCTG GTACAGACAA TATTCTGGGA AAAGCCCTGA

GTTGATAATG TTCATATACT CCAATGGTGA CAAAGAAGAT

GGAAGGTTTA CAGCACAGCT CAATAAAGCC AGCCAGTATG

TTTCTCTGCT CATCAGAGAC TCCCAGCCCA GTGATTCAGC

CACCTACCTC TGTGCCGTGA ACTTCGGAGG AGGAAAGCTT

ATCTTCGGAC AGGGAACGGA GTTATCTGTG AAACCCAAT

Known TCR-β:
Amino acid:
                                            (SEQ ID NO: 45)
MRIRLLCCVA FSLLWAGPVI AGITQAPTSQ ILAAGRRMTL

RCTQDMRHNA MYWYRQDLGL GLRLIHYSNT AGTTGKGEVP

DGYSVSRANT DDFPLTLASA VPSQTSVYFC ASSLSFGTEA

FFGQGTRLTV V
```

The transverse line is the CDR3 sequence, which is a sequence to be substituted

```
Substituted TCR-β:
                                            (SEQ ID NO: 46)
MRIRLLCCVA FSLLWAGPVI AGITQAPTSQ ILAAGRRMTL

RCTQDMRHNA MYWYRQDLGL GLRLIHYSNT AGTTGKGEVP

DGYSVSRANT DDFPLTLASA VPSQTSVYF CASSLGGSTPLHF

GQGTRLTV V
```

The transverse line is the substituted CDR3 sequence.

7. Detection of Knockout Efficiency of Original TCR

Figure 6A:
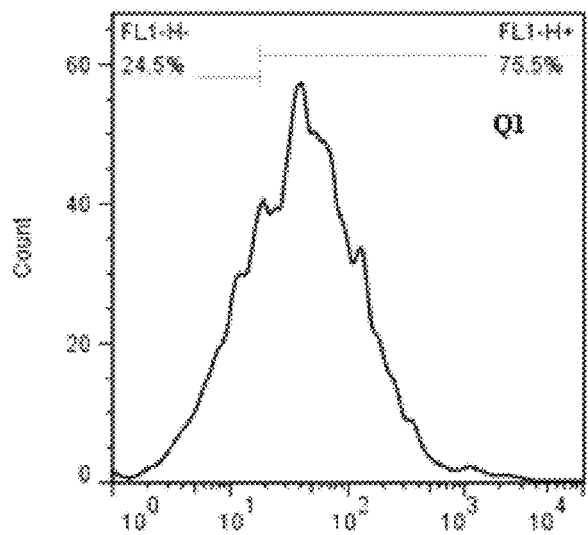
FIG. 6A shows knockout efficiency detection of the original TCR before knockout.
Figure 6B:
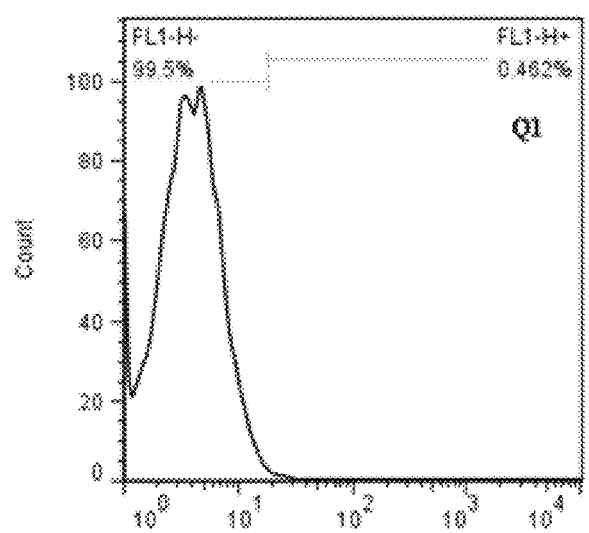
FIG. 6B shows knockout efficiency detection of the original TCR after knockout.

The CRISPR technology is used to knock out the original TCR on the PBMC. The result is as shown in FIGS. 6A & 6B. It can effectively reduce the expression of the original TCR. At this time, the transfection of the expression-specific TCR lentivirus can be performed.

8. Detection of Specific TCR Expression

Figure 7A:
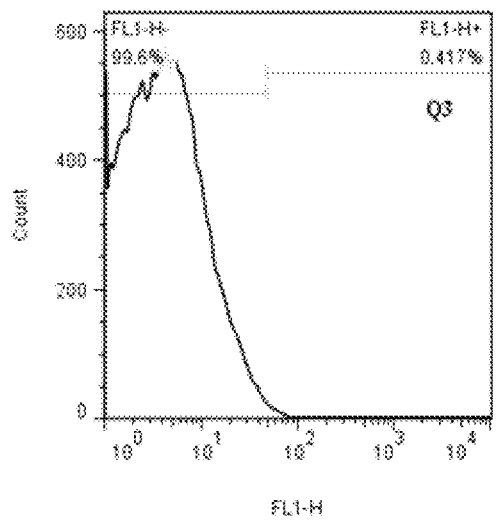
FIG. 7A shows the expression efficiency of specific TCR before transfection.
Figure 7B:
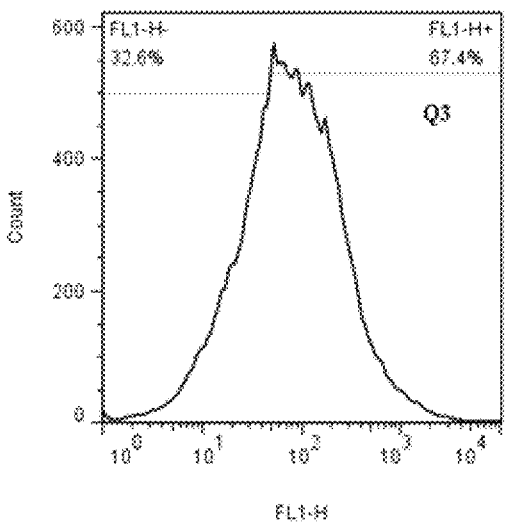
FIG. 7B shows the expression efficiency of specific TCR 7 days after transfection.

PBMC is transfected with lentiviruses that package specific TCR. On the seventh day, the expression efficiency of TCR is detected by flow cytometry. The results are as shown in FIGS. 7A & 7B. The constructed TCR can be expressed normally, and the ratio of TCR+ cells is 25.1%.

9. Blocking Efficiency of Immunosupressive Signaling Factor Antibody

Figure 8A:
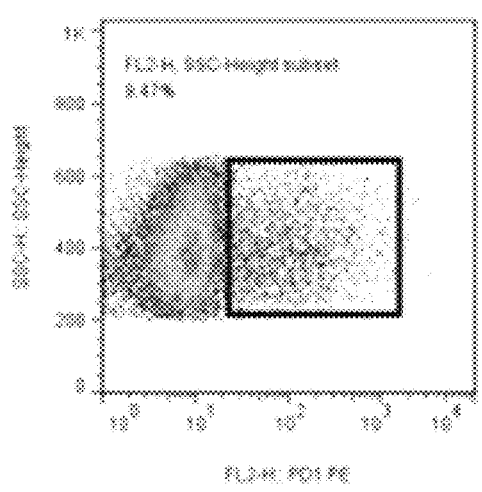
FIG. 8A shows the in vitro blocking effect of immunosuppressive signaling before blocking.
Figure 8B:
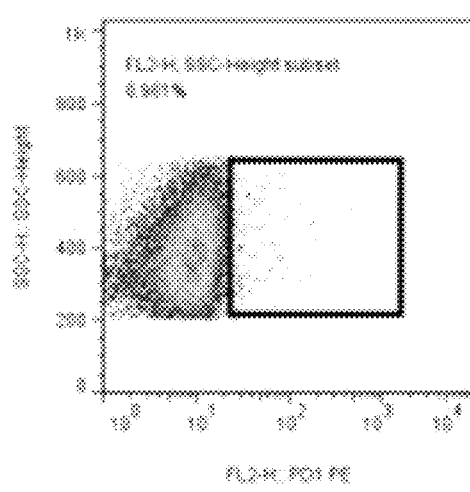
FIG. 8B shows the in vitro blocking effect of immunosuppressive signaling after blocking.

150 μg/mL of fluorescently labeled monoclonal antibody Keytruda is added to the PBS buffer system. As shown in FIGS. 8A & 8B, 90% of the cells are effectively blocked.

10. Killing Ability of the LRFFT2 Cell to Target Cells

Figure 9:
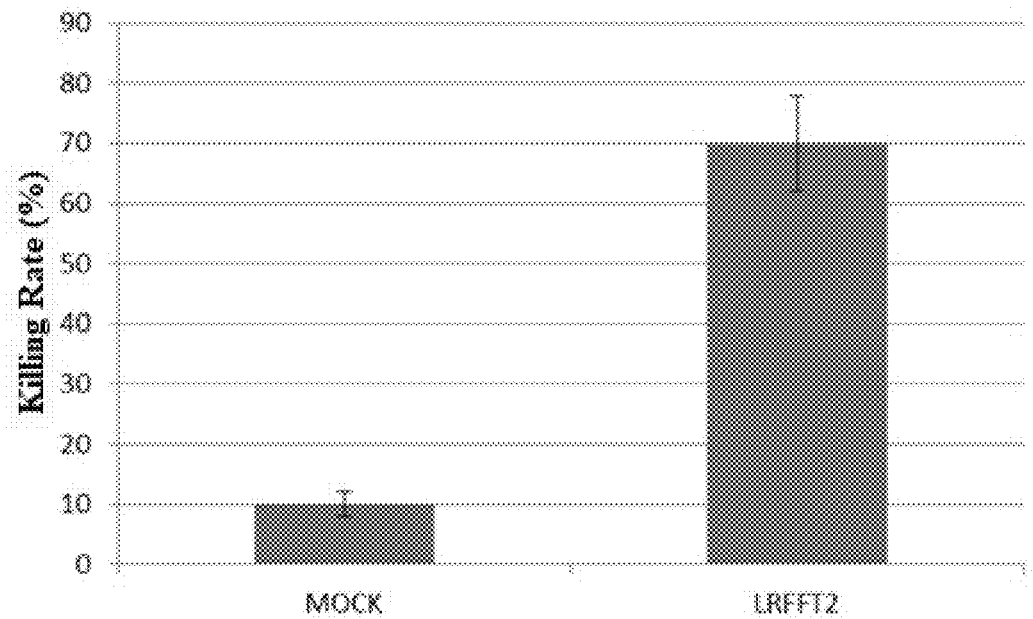
FIG. 9 shows LDH release detection of killing efficiency.

The control cell and the LRFFT2 cell are respectively used to detect the killing efficiency of the target cells derived from the mutant antigen epitope, and the untreated cells are used as the control (Mock), and the target ratio is set to be 40:1. The results are as shown in FIG. 9, and compared with the control group, the LRFFT2 cell has a strong killing effect on the target cells.

11. Detection of Cytokines Released by the LRFFT2 Cell

Figure 10:
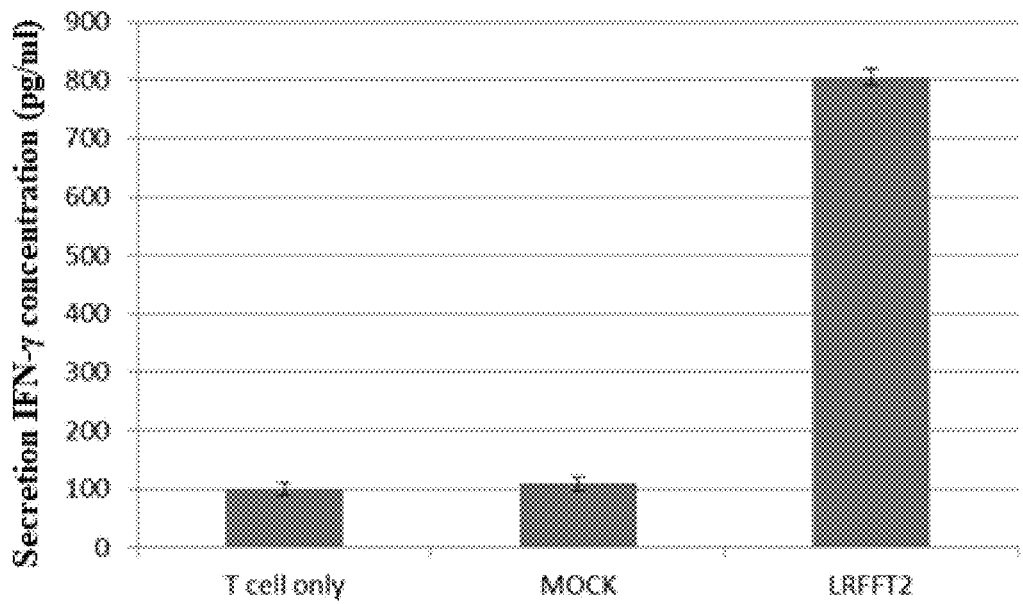
FIG. 10 shows ELISA detection of the release of cytokine

During co-culture of the tumor cells and the effector cells, mutant antigens on the tumor cells can be recognized due to the effector cells. Therefore, a series of cytokines are produced. IFN-γ is one of the most important cytokines in anti-tumor action. FIG. 10 shows the detection of the released IFN-γ when the LRFFT2 cell is co-cultured with tumor cells in a ratio of 1:1. The result shows that compared with IFN-γ produced by the effector cells (T cells only), after co-cultured with tumor cells, the LRFFT2 cell can produce more IFN-γ. This result is consistent with the results of the killing experiment, which indicates that T cells expressing the specific TCR, combined with knockout of an immunosupressive signaling factor, can more effectively enhance the anti-tumor ability.

Figure 11:
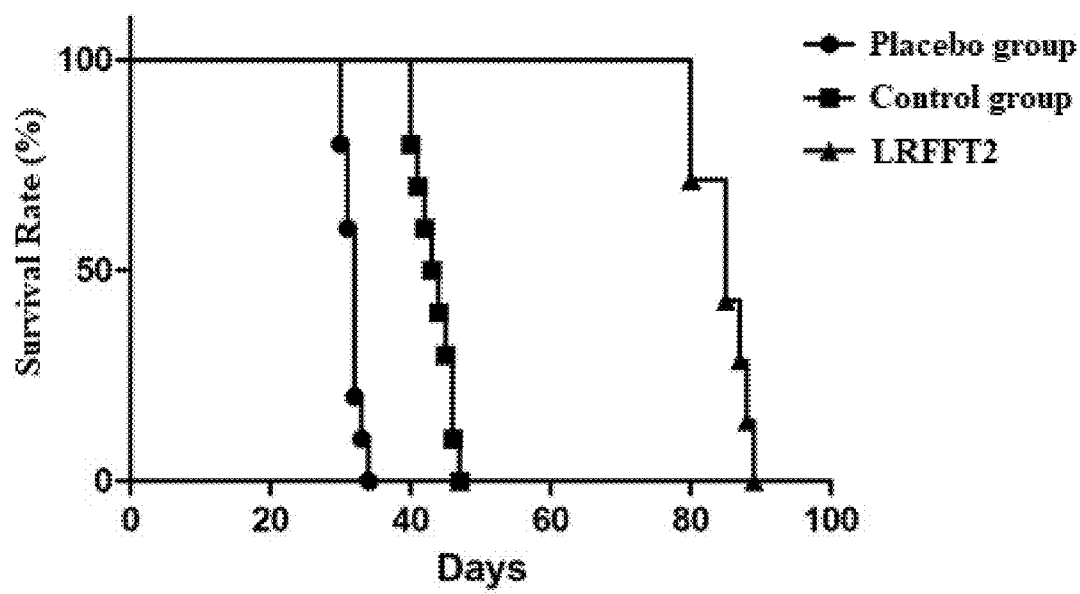
FIG. 11 shows a survival curve of an animal tumor-bearing model.

12. Construction of Specific Antigen-Expressing Target Cells and Tumor Model Survival Experiments A specific antigen-expressing tumor target cell line is successfully constructed, and a tumor-bearing animal model is established. The result (FIG. 11) shows that the LRFFT2 cell has a significant effect on the survival improvement of tumor-bearing mice.

13. Clinical Case:

A male patient: 55 years old. Diagnosis of disease: recurrence of intrahepatic cholangiocarcinoma after surgery. The first course of treatment: LRFFT2 cells once a month, the number of 1×109 cells, a total of 2 times. The second course of treatment: LRFFT2 cells once every six months, the number of 1×109 cells, a total of 2 times. At the end of the administration, there is no progression in 22 months.

Other cases:

| Patient No. | Disease diagnosis | Progress-free survival time |
|---|---|---|
| 1 | Gastric adenocarcinoma liver metastasis | 2017.3-present |
| 2 | Stomach cancer | 2017.3-present |
| 3 | Lung cancer | 2017.4-present |
| 4 | Adenocarcinoma of lung | 2017.4-present |
| 5 | Adenocarcinoma of lung | 2017.6-present |
| 6 | Esophagus cancer | 2017.6-present |

Note:
the meaning of "present" is "the day before the application date"

Various embodiments of the disclosure may have one or more the following effects. The LRFFT2 cell provided by the disclosure may be widely used in individualized precise treatment of solid tumors. The transformed T cells block immunosuppressive signaling molecules with antibodies in vitro may protect the specific killing T cells from inhibition in vivo and may improve the killing ability of T cells to tumor cells. The LRFFT2 cell may have more offensive and defensive effects. The LRFFT2 cell may be used in individualized precise treatment of solid tumors. The tumor antigen may be a mutant antigen different from other tissues. The tumor antigen may have a strong target specificity, may not be easy to cause off-target effects, and may have high safety. The proportion of the obtained specific cells may be high. The distribution of the specific cells capable of recognizing tumor antigens in PB MC may be 0.5% or less. The proportion of the cells transformed by the LRFFT2 scheme and the specific T cells (TCR+) recognizing the tumor antigens may be 70% or more. Since the LRFFT2 cell blocked the immunosuppressive targets such as PD1, CTLA4, TIM3, LAG3, etc., the killing ability against tumors may not be limited, and the killing efficiency may be higher.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The invention claimed is:

1. An LRFFT2 cell, prepared by a method comprising the steps of:
   1) using human peripheral blood for ctDNA sequencing or tumor tissues for whole exome sequencing, and screening out mutation sites;
   2) performing antigen epitope prediction according to the mutation sites, and synthesizing a gene sequence of mutant peptides;
   3) constructing a lentiviral vector expressing the mutant peptides, and packaging a lentivirus;
   4) transfecting an antigen-presenting cell and co-culturing with a Peripheral Blood Mononuclear Cell (PBMC) to obtain an LFF cell;
   5) stimulating the LFF cell with the mutant peptides as an antigen to screen out mutant polypeptides recognized by the LFF cell;
   6) stimulating the LFF cell with the mutant polypeptides recognized by the LFF cell as an antigen, screening out a specific cell capable of recognizing the mutant polypeptides recognized by the LFF cell, and sequencing and obtaining a high-frequency TCR gene of the specific cell, wherein the high-frequency TCR gene of the specific cell is TCR6 comprising the DNA sequence of SEQ ID NO: 23 and the amino acid sequence of SED ID NO: 24;
   7) knocking out an original TCR gene in peripheral blood T cells and transferring the TCR6 to obtain a TCR-T cell; and
   8) blocking a suppressive signaling molecule by an antibody in vitro, to obtain an LRFFT2 cell;
   wherein the suppressive signaling molecule comprises one or more of PD-1, Tim-3, LAG3, CTLA-4, BTLA, VISTA, CD160, and 2B4 (CD244).

2. The LRFFT2 cell according to claim 1, wherein:
a predicted antigen epitope is centered on a mutant amino acid site;
the predicted antigen epitope extends 8 amino acids to each side; and
a polypeptide segment having 17 amino acids is used as a potential antigen epitope.

3. The LRFFT2 cell according to claim 1, wherein:
IC50 of a potential antigen epitope is analyzed by using prediction software; and
if the IC50<1,000 nM, the potential antigen epitope is considered to be an antigen epitope.

4. The LRFFT2 cell according to claim 1, wherein the step 7) comprises knocking out the original TCR gene by CRISPR technology.

5. The LRFFT2 cell according to claim 1, wherein the antigen presenting cell comprises one or more of PBMC, a dendritic cell, neutrophil, B lymphocyte, and macrophage.

* * * * *

SEQUENCE LISTING

```
<160> NUMBER OF SEQ ID NOS: 46

<210> SEQ ID NO 1
<211> LENGTH: 9
<212> TYPE: PRT
<213> ORGANISM: artificial sequence
<220> FEATURE:
<223> OTHER INFORMATION: Antigen epitope prediction 1

<400> SEQUENCE: 1

Ser Ser Met Gln Thr Gly Met Asn Leu
1               5

<210> SEQ ID NO 2
<211> LENGTH: 8
<212> TYPE: PRT
<213> ORGANISM: artificial sequence
<220> FEATURE:
<223> OTHER INFORMATION: Antigen epitope prediction2

<400> SEQUENCE: 2

Ala Val Gly Lys His Thr Leu Lys
1               5

<210> SEQ ID NO 3
<211> LENGTH: 9
<212> TYPE: PRT
<213> ORGANISM: artificial sequence
<220> FEATURE:
<223> OTHER INFORMATION: Antigen epitope prediction3

<400> SEQUENCE: 3

Ile Val Ile Pro Asn Asp Gly Leu Tyr
1               5

<210> SEQ ID NO 4
<211> LENGTH: 11
<212> TYPE: PRT
<213> ORGANISM: artificial sequence
<220> FEATURE:
<223> OTHER INFORMATION: Antigen epitope prediction 4

<400> SEQUENCE: 4

Tyr Met Phe Gln Arg Asn Val Asn Ser Val Leu
1               5                   10

<210> SEQ ID NO 5
<211> LENGTH: 10
<212> TYPE: PRT
<213> ORGANISM: artificial sequence
<220> FEATURE:
<223> OTHER INFORMATION: Antigen epitope prediction 5

<400> SEQUENCE: 5
```

```
Ala Ser Asp Val Asp Tyr Cys Val Ala Lys
1               5                   10

<210> SEQ ID NO 6
<211> LENGTH: 10
<212> TYPE: PRT
<213> ORGANISM: artificial sequence
<220> FEATURE:
<223> OTHER INFORMATION: Antigen epitope prediction 6

<400> SEQUENCE: 6

Asn Met Ala Val Gly Lys His Thr Leu Lys
1               5                   10

<210> SEQ ID NO 7
<211> LENGTH: 10
<212> TYPE: PRT
<213> ORGANISM: artificial sequence
<220> FEATURE:
<223> OTHER INFORMATION: Antigen epitope prediction

<400> SEQUENCE: 7

Asn Met Ala Val Gly Lys His Thr Leu Lys
1               5                   10

<210> SEQ ID NO 8
<211> LENGTH: 8
<212> TYPE: PRT
<213> ORGANISM: artificial sequence
<220> FEATURE:
<223> OTHER INFORMATION: Antigen epitope prediction8

<400> SEQUENCE: 8

Val Leu Met Pro Thr Lys Ala Val
1               5

<210> SEQ ID NO 9
<211> LENGTH: 11
<212> TYPE: PRT
<213> ORGANISM: artificial sequence
<220> FEATURE:
<223> OTHER INFORMATION: Antigen epitope prediction 9

<400> SEQUENCE: 9

Thr Gln Phe Val Asn Val Thr Phe Gln Met Lys
1               5                   10

<210> SEQ ID NO 10
<211> LENGTH: 10
<212> TYPE: PRT
<213> ORGANISM: artificial sequence
<220> FEATURE:
<223> OTHER INFORMATION: Antigen epitope prediction 10

<400> SEQUENCE: 10

Gln Pro Ile Glu Trp Val Lys Asp Thr Tyr
1               5                   10

<210> SEQ ID NO 11
<211> LENGTH: 11
<212> TYPE: PRT
<213> ORGANISM: artificial sequence
<220> FEATURE:
<223> OTHER INFORMATION: Antigen epitope prediction 11

<400> SEQUENCE: 11

Gln Ala Ser Ser Pro Pro Val Gly Ile Pro Met
```

<210> SEQ ID NO 12
<211> LENGTH: 10
<212> TYPE: PRT
<213> ORGANISM: artificial sequence
<220> FEATURE:
<223> OTHER INFORMATION: Antigen epitope prediction

<400> SEQUENCE: 12

Lys Leu Ala Thr Arg Tyr Val Phe Gln Ile
1               5                   10

<210> SEQ ID NO 13
<211> LENGTH: 39
<212> TYPE: DNA
<213> ORGANISM: artificial sequence
<220> FEATURE:
<223> OTHER INFORMATION: CDR3 DNA sequence

<400> SEQUENCE: 13
tgtgccagca gtctcaccct cacctacgag cagtacttc                               39

<210> SEQ ID NO 14
<211> LENGTH: 13
<212> TYPE: PRT
<213> ORGANISM: artificial sequence
<220> FEATURE:
<223> OTHER INFORMATION: CDR3 amino acid sequence

<400> SEQUENCE: 14

Cys Ala Ser Ser Leu Thr Leu Thr Tyr Glu Gln Tyr Phe
1               5                   10

<210> SEQ ID NO 15
<211> LENGTH: 36
<212> TYPE: DNA
<213> ORGANISM: artificial sequence
<220> FEATURE:
<223> OTHER INFORMATION: CDR3 DNA sequence

<400> SEQUENCE: 15
tgtgccagca gcaccgaaag acccgagcag tacttc                                  36

<210> SEQ ID NO 16
<211> LENGTH: 12
<212> TYPE: PRT
<213> ORGANISM: artificial sequence
<220> FEATURE:
<223> OTHER INFORMATION: CDR3 amino acid sequence

<400> SEQUENCE: 16

Cys Ala Ser Ser Thr Glu Arg Pro Glu Gln Tyr Phe
1               5                   10

<210> SEQ ID NO 17
<211> LENGTH: 45
<212> TYPE: DNA
<213> ORGANISM: artificial sequence
<220> FEATURE:
<223> OTHER INFORMATION: CDR3 DNA sequence

<400> SEQUENCE: 17
tgtgccagta gtattggggc aggtttccat ctcgagcagt acttc                        45

<210> SEQ ID NO 18

```
<211> LENGTH: 15
<212> TYPE: PRT
<213> ORGANISM: artificial sequence
<220> FEATURE:
<223> OTHER INFORMATION: CDR3 amino acid sequence

<400> SEQUENCE: 18

Cys Ala Ser Ser Ile Gly Ala Gly Phe His Leu Glu Gln Tyr Phe
1               5                   10                  15

<210> SEQ ID NO 19
<211> LENGTH: 42
<212> TYPE: DNA
<213> ORGANISM: artificial sequence
<220> FEATURE:
<223> OTHER INFORMATION: CDR3 DNA sequence

<400> SEQUENCE: 19
tgtgccagca gtttatcggc gggactgggt gagcagtact tc                          42

<210> SEQ ID NO 20
<211> LENGTH: 14
<212> TYPE: PRT
<213> ORGANISM: artificial sequence
<220> FEATURE:
<223> OTHER INFORMATION: CDR3 amino acid sequence

<400> SEQUENCE: 20

Cys Ala Ser Ser Leu Ser Ala Gly Leu Gly Glu Gln Tyr Phe
1               5                   10

<210> SEQ ID NO 21
<211> LENGTH: 39
<212> TYPE: DNA
<213> ORGANISM: artificial sequence
<220> FEATURE:
<223> OTHER INFORMATION: CDR3 DNA sequence

<400> SEQUENCE: 21
tgtgccagca gtgattggcc cttgaatgag cagttcttc                              39

<210> SEQ ID NO 22
<211> LENGTH: 13
<212> TYPE: PRT
<213> ORGANISM: artificial sequence
<220> FEATURE:
<223> OTHER INFORMATION: CDR3 amino acid sequence

<400> SEQUENCE: 22

Cys Ala Ser Ser Asp Trp Pro Leu Asn Glu Gln Phe Phe
1               5                   10

<210> SEQ ID NO 23
<211> LENGTH: 39
<212> TYPE: DNA
<213> ORGANISM: artificial sequence
<220> FEATURE:
<223> OTHER INFORMATION: CDR3 DNA sequence

<400> SEQUENCE: 23
tgtgccagca gtttgggggg gtcgacaccc ctccacttt                              39

<210> SEQ ID NO 24
<211> LENGTH: 13
<212> TYPE: PRT
<213> ORGANISM: artificial sequence
<220> FEATURE:
```

<223> OTHER INFORMATION: CDR3 amino acid sequence

<400> SEQUENCE: 24

Cys Ala Ser Ser Leu Gly Gly Ser Thr Pro Leu His Phe
1               5                   10

<210> SEQ ID NO 25
<211> LENGTH: 48
<212> TYPE: DNA
<213> ORGANISM: artificial sequence
<220> FEATURE:
<223> OTHER INFORMATION: CDR3 DNA sequence

<400> SEQUENCE: 25
tgtgccagca gtttggcggg agggcctagc acagatacgc agtatttt                    48

<210> SEQ ID NO 26
<211> LENGTH: 16
<212> TYPE: PRT
<213> ORGANISM: artificial sequence
<220> FEATURE:
<223> OTHER INFORMATION: CDR3 amino acid sequence

<400> SEQUENCE: 26

Cys Ala Ser Ser Leu Ala Gly Gly Pro Ser Thr Asp Thr Gln Tyr Phe
1               5                   10                  15

<210> SEQ ID NO 27
<211> LENGTH: 51
<212> TYPE: DNA
<213> ORGANISM: artificial sequence
<220> FEATURE:
<223> OTHER INFORMATION: CDR3 DNA sequence

<400> SEQUENCE: 27
tgcgccagca gcccagcgag aatcgggggg agcacagata cgcagtattt t                51

<210> SEQ ID NO 28
<211> LENGTH: 17
<212> TYPE: PRT
<213> ORGANISM: artificial sequence
<220> FEATURE:
<223> OTHER INFORMATION: CDR3 amino acid sequence

<400> SEQUENCE: 28

Cys Ala Ser Ser Pro Ala Arg Ile Gly Gly Ser Thr Asp Thr Gln Tyr
1               5                   10                  15

Phe

<210> SEQ ID NO 29
<211> LENGTH: 42
<212> TYPE: DNA
<213> ORGANISM: artificial sequence
<220> FEATURE:
<223> OTHER INFORMATION: CDR3 DNA sequence

<400> SEQUENCE: 29
tgcgccagca gccagacagg ggcgaactcc gagcagtact tc                          42

<210> SEQ ID NO 30
<211> LENGTH: 14
<212> TYPE: PRT
<213> ORGANISM: artificial sequence
<220> FEATURE:
<223> OTHER INFORMATION: CDR3 amino acid sequence

```
<400> SEQUENCE: 30

Cys Ala Ser Ser Gln Thr Gly Ala Asn Ser Glu Gln Tyr Phe
1               5                   10

<210> SEQ ID NO 31
<211> LENGTH: 42
<212> TYPE: DNA
<213> ORGANISM: artificial sequence
<220> FEATURE:
<223> OTHER INFORMATION: CDR3 DNA sequence

<400> SEQUENCE: 31
tgtgccagca gtgaaggcgg ggacaccggg gagctgtttt tt                              42

<210> SEQ ID NO 32
<211> LENGTH: 14
<212> TYPE: PRT
<213> ORGANISM: artificial sequence
<220> FEATURE:
<223> OTHER INFORMATION: CDR3 amino acid sequence

<400> SEQUENCE: 32

Cys Ala Ser Ser Glu Gly Gly Asp Thr Gly Glu Leu Phe Phe
1               5                   10

<210> SEQ ID NO 33
<211> LENGTH: 39
<212> TYPE: DNA
<213> ORGANISM: artificial sequence
<220> FEATURE:
<223> OTHER INFORMATION: CDR3 DNA sequence

<400> SEQUENCE: 33
tgtgccagca gcgtaggggg ggattatggc tacaccttc                                  39

<210> SEQ ID NO 34
<211> LENGTH: 13
<212> TYPE: PRT
<213> ORGANISM: artificial sequence
<220> FEATURE:
<223> OTHER INFORMATION: CDR3 amino acid sequence

<400> SEQUENCE: 34

Cys Ala Ser Ser Val Gly Gly Asp Tyr Gly Tyr Thr Phe
1               5                   10

<210> SEQ ID NO 35
<211> LENGTH: 39
<212> TYPE: DNA
<213> ORGANISM: artificial sequence
<220> FEATURE:
<223> OTHER INFORMATION: CDR3 DNA sequence

<400> SEQUENCE: 35
tgtgccagca gcttatcgga gggtactgaa gctttcttt                                  39

<210> SEQ ID NO 36
<211> LENGTH: 13
<212> TYPE: PRT
<213> ORGANISM: artificial sequence
<220> FEATURE:
<223> OTHER INFORMATION: CDR3 amino acid sequence

<400> SEQUENCE: 36

Cys Ala Ser Ser Leu Ser Glu Gly Thr Glu Ala Phe Phe
1               5                   10
```

```
<210> SEQ ID NO 37
<211> LENGTH: 45
<212> TYPE: DNA
<213> ORGANISM: artificial sequence
<220> FEATURE:
<223> OTHER INFORMATION: CDR3 DNA sequence

<400> SEQUENCE: 37
tgtgccagca gcttcccgga tgagggggac tatggctaca ccttc         45

<210> SEQ ID NO 38
<211> LENGTH: 15
<212> TYPE: PRT
<213> ORGANISM: artificial sequence
<220> FEATURE:
<223> OTHER INFORMATION: CDR3 amino acid sequence

<400> SEQUENCE: 38

Cys Ala Ser Ser Phe Pro Asp Glu Gly Asp Tyr Gly Tyr Thr Phe
1               5                   10                  15

<210> SEQ ID NO 39
<211> LENGTH: 51
<212> TYPE: DNA
<213> ORGANISM: artificial sequence
<220> FEATURE:
<223> OTHER INFORMATION: CDR3 DNA sequence

<400> SEQUENCE: 39
tgcagcgttg tggcactagc gggagggcgg acctcctacg agcagtactt c       51

<210> SEQ ID NO 40
<211> LENGTH: 17
<212> TYPE: PRT
<213> ORGANISM: artificial sequence
<220> FEATURE:
<223> OTHER INFORMATION: CDR3 amino acid sequence

<400> SEQUENCE: 40

Cys Ser Val Val Ala Leu Ala Gly Gly Arg Thr Ser Tyr Glu Gln Tyr
1               5                   10                  15

Phe

<210> SEQ ID NO 41
<211> LENGTH: 51
<212> TYPE: DNA
<213> ORGANISM: artificial sequence
<220> FEATURE:
<223> OTHER INFORMATION: CDR3 DNA sequence

<400> SEQUENCE: 41
tgtgccagct caccacggga caggggggctt actaactatg gctacacctt c       51

<210> SEQ ID NO 42
<211> LENGTH: 17
<212> TYPE: PRT
<213> ORGANISM: artificial sequence
<220> FEATURE:
<223> OTHER INFORMATION: CDR3 amino acid sequence

<400> SEQUENCE: 42

Cys Ala Ser Ser Pro Arg Asp Arg Gly Leu Thr Asn Tyr Gly Tyr Thr
1               5                   10                  15

Phe
```

<210> SEQ ID NO 43
<211> LENGTH: 133
<212> TYPE: PRT
<213> ORGANISM: artificial sequence
<220> FEATURE:
<223> OTHER INFORMATION: Known TCR-a amino acid sequence

<400> SEQUENCE: 43

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Phe Gly Gly Gly Lys Leu Ile Phe Gly Gln Gly Thr Glu Leu
        115                 120                 125

Ser Val Lys Pro Asn
    130
```

<210> SEQ ID NO 44
<211> LENGTH: 399
<212> TYPE: DNA
<213> ORGANISM: artificial sequence
<220> FEATURE:
<223> OTHER INFORMATION: Known TCR-a base sequence

<400> SEQUENCE: 44

```
atgatgaaat ccttgagagt tttactagtg atcctgtggc ttcagttgag ctgggtttgg     60
agccaacaga aggaggtgga gcagaattct ggacccctca gtgttccaga gggagccatt    120
gcctctctca actgcactta cagtgaccga ggttccagt ccttcttctg gtacagacaa    180
tattctggga aaagccctga gttgataatg ttcatatact ccaatggtga caaagaagat    240
ggaaggttta cagcacagct caataaagcc agccagtatg tttctctgct catcagagac    300
tcccagccca gtgattcagc cacctacctc tgtgccgtga acttcggagg aggaaagctt    360
atcttcggac agggaacgga gttatctgtg aaacccaat                           399
```

<210> SEQ ID NO 45
<211> LENGTH: 131
<212> TYPE: PRT
<213> ORGANISM: artificial sequence
<220> FEATURE:
<223> OTHER INFORMATION: Known TCR-b amino acid sequence

<400> SEQUENCE: 45

```
Met Arg Ile Arg Leu Leu Cys Cys Val Ala Phe Ser Leu Leu Trp Ala
1               5                   10                  15

Gly Pro Val Ile Ala Gly Ile Thr Gln Ala Pro Thr Ser Gln Ile Leu
            20                  25                  30

Ala Ala Gly Arg Arg Met Thr Leu Arg Cys Thr Gln Asp Met Arg His
```

```
                    35                  40                  45
Asn Ala Met Tyr Trp Tyr Arg Gln Asp Leu Gly Leu Gly Leu Arg Leu
        50                  55                  60

Ile His Tyr Ser Asn Thr Ala Gly Thr Thr Gly Lys Gly Glu Val Pro
65                  70                  75                  80

Asp Gly Tyr Ser Val Ser Arg Ala Asn Thr Asp Asp Phe Pro Leu Thr
                85                  90                  95

Leu Ala Ser Ala Val Pro Ser Gln Thr Ser Val Tyr Phe Cys Ala Ser
            100                 105                 110

Ser Leu Ser Phe Gly Thr Glu Ala Phe Phe Gly Gln Gly Thr Arg Leu
        115                 120                 125

Thr Val Val
        130

<210> SEQ ID NO 46
<211> LENGTH: 131
<212> TYPE: PRT
<213> ORGANISM: artificial sequence
<220> FEATURE:
<223> OTHER INFORMATION: substituted  TCR-b amino acid sequence

<400> SEQUENCE: 46

Met Arg Ile Arg Leu Leu Cys Cys Val Ala Phe Ser Leu Leu Trp Ala
1               5                   10                  15

Gly Pro Val Ile Ala Gly Ile Thr Gln Ala Pro Thr Ser Gln Ile Leu
                20                  25                  30

Ala Ala Gly Arg Arg Met Thr Leu Arg Cys Thr Gln Asp Met Arg His
            35                  40                  45

Asn Ala Met Tyr Trp Tyr Arg Gln Asp Leu Gly Leu Gly Leu Arg Leu
        50                  55                  60

Ile His Tyr Ser Asn Thr Ala Gly Thr Thr Gly Lys Gly Glu Val Pro
65                  70                  75                  80

Asp Gly Tyr Ser Val Ser Arg Ala Asn Thr Asp Asp Phe Pro Leu Thr
                85                  90                  95

Leu Ala Ser Ala Val Pro Ser Gln Thr Ser Val Tyr Phe Cys Ala Ser
            100                 105                 110

Ser Leu Gly Gly Ser Thr Pro Leu His Phe Gly Gln Gly Thr Arg Leu
        115                 120                 125

Thr Val Val
        130
```